(12) United States Patent
Baker, Jr.

(10) Patent No.: US 8,280,469 B2
(45) Date of Patent: Oct. 2, 2012

(54) METHOD FOR DETECTION OF ABERRANT TISSUE SPECTRA

(75) Inventor: Clark R. Baker, Jr., Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1597 days.

(21) Appl. No.: 11/716,777

(22) Filed: Mar. 9, 2007

(65) Prior Publication Data
US 2008/0221414 A1    Sep. 11, 2008

(51) Int. Cl.
A61B 5/1455    (2006.01)
(52) U.S. Cl. .................. 600/310; 600/322; 600/323
(58) Field of Classification Search .................. 600/310, 600/322, 323, 340
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 3,998,550 A | 12/1976 | Konishi et al. |
| 4,066,068 A | 1/1978 | Nilsson et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,364,008 A | 12/1982 | Jacques |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |

(Continued)

FOREIGN PATENT DOCUMENTS
CA    2353007 A1    6/2000
(Continued)

OTHER PUBLICATIONS

U.S. Appl. No. 11/528,154, filed Sep. 27, 2006, Debreczeny, et al.

(Continued)

*Primary Examiner* — Eric Winakur
*Assistant Examiner* — Chu Chuan (JJ) Liu

(57) ABSTRACT

A method is provided for determining contact of a sensor with a patient's tissue. The method comprises comparing the intensity of detected light at a first wavelength to a threshold, wherein the first wavelength is not used to determine a physiological characteristic of the patient, and determining if the sensor is in contact with the patient's tissue based on the comparison. In addition, a method is provided for determining the amount of light shunting during operation of the sensor. The method comprises comparing the intensity of detected light at a first wavelength to a threshold, wherein the first wavelength is not used to determine a physiological characteristic of the patient, and determining the amount of light shunting based on the comparison.

21 Claims, 5 Drawing Sheets

U.S. PATENT DOCUMENTS

| | | |
|---|---|---|
| 4,700,708 A | 10/1987 | New, Jr. et al. |
| 4,711,244 A | 12/1987 | Kuzara |
| 4,714,080 A | 12/1987 | Edgar, Jr. et al. |
| 4,714,341 A | 12/1987 | Hamaguri et al. |
| 4,722,120 A | 2/1988 | Lu |
| 4,723,554 A | 2/1988 | Oman et al. |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,365 A | 2/1989 | Bastian |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,850,365 A | 7/1989 | Rosenthal |
| 4,854,699 A | 8/1989 | Edgar, Jr. |
| 4,859,056 A | 8/1989 | Prosser et al. |
| 4,859,057 A | 8/1989 | Taylor et al. |
| 4,860,753 A | 8/1989 | Amerena |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,907,594 A | 3/1990 | Muz |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,057,695 A | 10/1991 | Hirao et al. |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,086,781 A | 2/1992 | Bookspan |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H0001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,146,091 A | 9/1992 | Knudson |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,277,181 A | 1/1994 | Mendelson et al. |
| 5,278,627 A | 1/1994 | Aoyagi et al. |
| 5,279,295 A | 1/1994 | Martens et al. |
| 5,282,467 A | 2/1994 | Piantadosi et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,337,745 A | 8/1994 | Benaron |
| 5,337,937 A | 8/1994 | Remiszewski et al. |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |

| | | |
|---|---|---|
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,674 A | 1/1995 | Kuestner |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,615,689 A | 4/1997 | Kotler |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,721 A | 11/1997 | Kuhls |
| 5,687,722 A | 11/1997 | Tien et al. |
| 5,692,503 A | 12/1997 | Kuenstner |
| 5,692,505 A | 12/1997 | Fouts |
| 5,701,902 A | 12/1997 | Vari et al. |
| 5,709,205 A | 1/1998 | Bukta |
| 5,713,355 A | 2/1998 | Richardson et al. |
| 5,720,284 A | 2/1998 | Aoyagi et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,735,284 A | 4/1998 | Tsoglin et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,747,789 A | 5/1998 | Godik |
| 5,752,914 A | 5/1998 | DeLonzor et al. |
| 5,755,226 A | 5/1998 | Carim et al. |
| 5,755,672 A | 5/1998 | Arai et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,788,643 A | 8/1998 | Feldman |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |

| | | | | | |
|---|---|---|---|---|---|
| 5,803,908 A | 9/1998 | Steuer et al. | 5,997,343 A | 12/1999 | Mills et al. |
| 5,803,910 A | 9/1998 | Potratz | 5,999,834 A | 12/1999 | Wang et al. |
| 5,807,246 A | 9/1998 | Sakaguchi et al. | 6,002,952 A | 12/1999 | Diab et al. |
| 5,807,247 A | 9/1998 | Merchant et al. | 6,005,658 A | 12/1999 | Kaluza et al. |
| 5,807,248 A | 9/1998 | Mills | 6,006,120 A | 12/1999 | Levin |
| 5,810,723 A | 9/1998 | Aldrich | 6,011,985 A | 1/2000 | Athan et al. |
| 5,810,724 A | 9/1998 | Gronvall | 6,011,986 A | 1/2000 | Diab et al. |
| 5,813,980 A | 9/1998 | Levinson et al. | 6,014,576 A | 1/2000 | Raley et al. |
| 5,817,008 A | 10/1998 | Rafert et al. | 6,018,673 A | 1/2000 | Chin et al. |
| 5,817,009 A | 10/1998 | Rosenheimer et al. | 6,018,674 A | 1/2000 | Aronow |
| 5,817,010 A | 10/1998 | Hibl | 6,022,321 A | 2/2000 | Amano et al. |
| 5,818,985 A | 10/1998 | Merchant et al. | 6,023,541 A | 2/2000 | Merchant et al. |
| 5,820,550 A | 10/1998 | Polson et al. | 6,026,312 A | 2/2000 | Shemwell et al. |
| 5,823,950 A | 10/1998 | Diab et al. | 6,026,314 A | 2/2000 | Amerov et al. |
| 5,823,952 A | 10/1998 | Levinson et al. | 6,031,603 A | 2/2000 | Fine et al. |
| 5,827,179 A | 10/1998 | Lichter et al. | 6,035,223 A | 3/2000 | Baker, Jr. |
| 5,827,181 A | 10/1998 | Dias et al. | 6,036,642 A | 3/2000 | Diab et al. |
| 5,827,182 A | 10/1998 | Raley et al. | 6,041,247 A | 3/2000 | Weckstrom et al. |
| 5,829,439 A | 11/1998 | Yokosawa et al. | 6,044,283 A | 3/2000 | Fein et al. |
| 5,830,135 A | 11/1998 | Bosque et al. | 6,047,201 A | 4/2000 | Jackson, III |
| 5,830,136 A | 11/1998 | DeLonzor et al. | 6,055,447 A | 4/2000 | Well |
| 5,830,137 A | 11/1998 | Scharf | 6,061,584 A | 5/2000 | Lovejoy et al. |
| 5,833,602 A | 11/1998 | Osemwota | 6,064,898 A | 5/2000 | Aldrich |
| 5,839,439 A | 11/1998 | Nierlich et al. | 6,064,899 A | 5/2000 | Fein et al. |
| RE36,000 E | 12/1998 | Swedlow et al. | 6,067,462 A | 5/2000 | Diab et al. |
| 5,842,979 A | 12/1998 | Jarman et al. | 6,073,038 A | 6/2000 | Wang et al. |
| 5,842,981 A | 12/1998 | Larsen et al. | 6,078,829 A | 6/2000 | Uchida |
| 5,842,982 A | 12/1998 | Mannheimer | 6,078,833 A | 6/2000 | Hueber |
| 5,846,190 A | 12/1998 | Woehrle | 6,081,735 A | 6/2000 | Diab et al. |
| 5,851,178 A | 12/1998 | Aronow | 6,083,157 A | 7/2000 | Noller |
| 5,851,179 A | 12/1998 | Ritson et al. | 6,083,172 A | 7/2000 | Baker, Jr. et al. |
| 5,853,364 A | 12/1998 | Baker, Jr. et al. | 6,088,607 A | 7/2000 | Diab et al. |
| 5,860,919 A | 1/1999 | Kiani-Azarbayjany et al. | 6,094,592 A | 7/2000 | Yorkey et al. |
| 5,865,736 A | 2/1999 | Baker, Jr. et al. | 6,095,974 A | 8/2000 | Shemwell et al. |
| 5,879,294 A | 3/1999 | Anderson et al. | 6,104,938 A | 8/2000 | Huiku et al. |
| 5,885,213 A | 3/1999 | Richardson et al. | 6,104,939 A | 8/2000 | Groner |
| 5,890,929 A | 4/1999 | Mills et al. | 6,112,107 A | 8/2000 | Hannula |
| 5,891,021 A | 4/1999 | Dillon et al. | 6,113,541 A | 9/2000 | Dias et al. |
| 5,891,022 A | 4/1999 | Pologe | 6,115,621 A | 9/2000 | Chin |
| 5,891,024 A | 4/1999 | Jarman et al. | 6,122,535 A | 9/2000 | Kaestle et al. |
| 5,891,025 A | 4/1999 | Buschmann et al. | 6,125,297 A | 9/2000 | Siconolfi |
| 5,891,026 A | 4/1999 | Wang et al. | 6,133,994 A | 10/2000 | Mathews et al. |
| 5,902,235 A | 5/1999 | Lewis et al. | 6,135,952 A | 10/2000 | Coetzee |
| 5,906,582 A | 5/1999 | Kondo et al. | 6,144,444 A | 11/2000 | Haworth et al. |
| 5,910,108 A | 6/1999 | Solenberger | 6,144,867 A | 11/2000 | Walker et al. |
| 5,911,690 A | 6/1999 | Rall | 6,144,868 A | 11/2000 | Parker |
| 5,912,656 A | 6/1999 | Tham et al. | 6,149,481 A | 11/2000 | Wang et al. |
| 5,913,819 A | 6/1999 | Taylor et al. | 6,149,591 A | 11/2000 | Henderson et al. |
| 5,916,154 A | 6/1999 | Hobbs et al. | 6,151,107 A | 11/2000 | Schöllermann et al. |
| 5,916,155 A | 6/1999 | Levinson et al. | 6,151,516 A | 11/2000 | Kiani-Azarbayjany et al. |
| 5,919,133 A | 7/1999 | Taylor et al. | 6,151,518 A | 11/2000 | Hayashi |
| 5,919,134 A | 7/1999 | Diab | 6,152,754 A | 11/2000 | Gerhardt et al. |
| 5,920,263 A | 7/1999 | Huttenhoff et al. | 6,154,667 A | 11/2000 | Miura et al. |
| 5,921,921 A | 7/1999 | Potratz et al. | 6,157,850 A | 12/2000 | Diab et al. |
| 5,922,607 A | 7/1999 | Bernreuter | 6,159,147 A | 12/2000 | Lichter |
| 5,924,979 A | 7/1999 | Swedlow et al. | 6,163,715 A | 12/2000 | Larsen et al. |
| 5,924,980 A | 7/1999 | Coetzee | 6,165,005 A | 12/2000 | Mills et al. |
| 5,924,982 A | 7/1999 | Chin | 6,173,196 B1 | 1/2001 | Delonzor et al. |
| 5,924,985 A | 7/1999 | Jones | 6,178,342 B1 | 1/2001 | Thompson et al. |
| 5,934,277 A | 8/1999 | Mortz | 6,178,343 B1 | 1/2001 | Bindszus et al. |
| 5,934,925 A | 8/1999 | Tobler et al. | 6,179,159 B1 | 1/2001 | Gurley |
| 5,940,182 A | 8/1999 | Lepper, Jr. et al. | 6,181,958 B1 | 1/2001 | Steuer et al. |
| 5,954,644 A | 9/1999 | Dettling et al. | 6,181,959 B1 | 1/2001 | Schöllermann et al. |
| 5,957,840 A | 9/1999 | Terasawa et al. | 6,184,521 B1 | 2/2001 | Coffin, IV et al. |
| 5,960,610 A | 10/1999 | Levinson et al. | 6,188,470 B1 | 2/2001 | Grace |
| 5,961,450 A | 10/1999 | Merchant et al. | 6,192,260 B1 | 2/2001 | Chance |
| 5,961,452 A | 10/1999 | Chung et al. | 6,195,575 B1 | 2/2001 | Levinson |
| 5,964,701 A | 10/1999 | Asada et al. | 6,198,951 B1 | 3/2001 | Kosuda et al. |
| 5,971,930 A | 10/1999 | Elghazzawi | 6,206,830 B1 | 3/2001 | Diab et al. |
| 5,978,691 A | 11/1999 | Mills | 6,213,952 B1 | 4/2001 | Finarov et al. |
| 5,978,693 A | 11/1999 | Hamilton et al. | 6,217,523 B1 | 4/2001 | Amano et al. |
| 5,983,120 A | 11/1999 | Groner et al. | 6,222,189 B1 | 4/2001 | Misner et al. |
| 5,983,122 A | 11/1999 | Jarman et al. | 6,223,064 B1 | 4/2001 | Lynn |
| 5,987,343 A | 11/1999 | Kinast | 6,226,539 B1 | 5/2001 | Potratz |
| 5,991,648 A | 11/1999 | Levin | 6,226,540 B1 | 5/2001 | Bernreuter et al. |
| 5,995,855 A | 11/1999 | Kiani et al. | 6,229,856 B1 | 5/2001 | Diab et al. |
| 5,995,856 A | 11/1999 | Mannheimer et al. | 6,230,035 B1 | 5/2001 | Aoyagi et al. |
| 5,995,858 A | 11/1999 | Kinast | 6,233,470 B1 | 5/2001 | Tsuchiya |
| 5,995,859 A | 11/1999 | Takahashi | 6,236,871 B1 | 5/2001 | Tsuchiya |

| | | |
|---|---|---|
| 6,236,872 B1 | 5/2001 | Diab et al. |
| 6,240,305 B1 | 5/2001 | Tsuchiya |
| 6,246,894 B1 | 6/2001 | Steuer et al. |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,280,396 B1 | 8/2001 | Clark et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,336,044 B1 | 1/2002 | Ghiassi et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,370,426 B1 | 4/2002 | Campbell et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,442,408 B1 | 8/2002 | Wenzel et al. |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,807 B1 | 10/2002 | Dobson et al. |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,488,677 B1 | 12/2002 | Bowman et al. |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,936 B1 | 1/2003 | Monfre et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,592,574 B1 | 7/2003 | Shimmick et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,600,946 B1 | 7/2003 | Rice |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,635,491 B1 | 10/2003 | Khalil et al. |
| 6,636,759 B2 | 10/2003 | Robinson |
| 6,640,116 B2 | 10/2003 | Diab |
| 6,643,530 B2 | 11/2003 | Diab et al. |
| 6,643,531 B1 | 11/2003 | Katarow |
| 6,643,543 B2 | 11/2003 | Takehara et al. |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |

| Patent | Kind | Date | Name |
|---|---|---|---|
| 6,653,618 | B2 | 11/2003 | Zenzie |
| 6,654,620 | B2 | 11/2003 | Wu et al. |
| 6,654,621 | B2 | 11/2003 | Palatnik et al. |
| 6,654,622 | B1 | 11/2003 | Eberhard et al. |
| 6,654,623 | B1 | 11/2003 | Kästle |
| 6,654,624 | B2 | 11/2003 | Diab et al. |
| 6,658,276 | B2 | 12/2003 | Kianl et al. |
| 6,658,277 | B2 | 12/2003 | Wassermann |
| 6,662,033 | B2 | 12/2003 | Casciani et al. |
| 6,665,551 | B1 | 12/2003 | Suzuki |
| 6,668,181 | B2 | 12/2003 | Wenzel et al. |
| 6,668,182 | B2 | 12/2003 | Hubelbank |
| 6,668,183 | B2 | 12/2003 | Hicks et al. |
| 6,671,526 | B1 | 12/2003 | Aoyagi et al. |
| 6,671,528 | B2 | 12/2003 | Steuer et al. |
| 6,671,530 | B2 | 12/2003 | Chung et al. |
| 6,671,531 | B2 | 12/2003 | Al-Ali et al. |
| 6,671,532 | B1 | 12/2003 | Fudge et al. |
| 6,675,029 | B2 | 1/2004 | Monfre et al. |
| 6,675,031 | B1 | 1/2004 | Porges et al. |
| 6,678,543 | B2 | 1/2004 | Diab et al. |
| 6,681,126 | B2 | 1/2004 | Solenberger |
| 6,681,128 | B2 | 1/2004 | Steuer et al. |
| 6,681,454 | B2 | 1/2004 | Modgil et al. |
| 6,684,090 | B2 | 1/2004 | Ali et al. |
| 6,684,091 | B2 | 1/2004 | Parker |
| 6,687,519 | B2 | 2/2004 | Steuer et al. |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,712,762 | B1 | 3/2004 | Lichter |
| 6,714,803 | B1 | 3/2004 | Mortz |
| 6,714,804 | B2 | 3/2004 | Al-Ali et al. |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,725,074 | B1 | 4/2004 | Kästle |
| 6,725,075 | B2 | 4/2004 | Al-Ali |
| 6,731,962 | B1 | 5/2004 | Katarow |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 | 6/2004 | Hicks et al. |
| 6,748,253 | B2 | 6/2004 | Norris et al. |
| 6,748,254 | B2 | 6/2004 | O'Neill et al. |
| 6,754,515 | B1 | 6/2004 | Pologe |
| 6,754,516 | B2 | 6/2004 | Mannheimer |
| 6,760,607 | B2 | 7/2004 | Al-Ali |
| 6,760,609 | B2 | 7/2004 | Jacques |
| 6,760,610 | B2 | 7/2004 | Tschupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,777,240 | B2 | 8/2004 | Hazen et al. |
| 6,778,923 | B2 | 8/2004 | Norris et al. |
| 6,780,158 | B2 | 8/2004 | Yarita |
| 6,791,689 | B1 | 9/2004 | Weckstrom |
| 6,792,300 | B1 | 9/2004 | Diab et al. |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab et al. |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills et al. |
| 6,836,679 | B2 | 12/2004 | Baker, Jr. et al. |
| 6,839,579 | B1 | 1/2005 | Chin |
| 6,839,580 | B2 | 1/2005 | Zonios et al. |
| 6,839,582 | B2 | 1/2005 | Heckel |
| 6,839,659 | B2 | 1/2005 | Tarassenko et al. |
| 6,842,635 | B1 | 1/2005 | Parker |
| 6,845,256 | B2 | 1/2005 | Chin et al. |
| 6,849,046 | B2 | 2/2005 | Eyal-Bickels |
| 6,850,787 | B2 | 2/2005 | Weber et al. |
| 6,850,788 | B2 | 2/2005 | Al-Ali |
| 6,850,789 | B2 | 2/2005 | Schweitzer, Jr. et al. |
| 6,861,639 | B2 | 3/2005 | Al-Ali |
| 6,863,652 | B2 | 3/2005 | Huang et al. |
| 6,865,407 | B2 | 3/2005 | Kimball et al. |
| 6,873,865 | B2 | 3/2005 | Steuer et al. |
| 6,879,850 | B2 | 4/2005 | Kimball |
| 6,882,874 | B2 | 4/2005 | Huiku |
| 6,898,452 | B2 | 5/2005 | Al-Ali et al. |
| 6,909,912 | B2 | 6/2005 | Melker et al. |
| 6,912,413 | B2 | 6/2005 | Rantala et al. |
| 6,916,289 | B2 | 7/2005 | Schnall |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,941,162 | B2 | 9/2005 | Fudge et al. |
| 6,947,781 | B2 | 9/2005 | Asada et al. |
| 6,950,687 | B2 | 9/2005 | Al-Ali |
| 6,950,699 | B1 | 9/2005 | Manwaring et al. |
| 6,954,664 | B2 | 10/2005 | Sweitzer |
| 6,963,767 | B2 | 11/2005 | Rantala et al. |
| 6,968,221 | B2 | 11/2005 | Rosenthal |
| 6,971,580 | B2 | 12/2005 | Zhu et al. |
| 6,979,812 | B2 | 12/2005 | Al-Ali |
| 6,983,178 | B2 | 1/2006 | Fine et al. |
| 6,985,763 | B2 | 1/2006 | Boas et al. |
| 6,985,764 | B2 | 1/2006 | Mason et al. |
| 6,990,426 | B2 | 1/2006 | Yoon et al. |
| 6,992,751 | B2 | 1/2006 | Okita et al. |
| 6,992,772 | B2 | 1/2006 | Block et al. |
| 6,993,371 | B2 | 1/2006 | Kiani et al. |
| 6,993,372 | B2 | 1/2006 | Fine et al. |
| 6,996,427 | B2 | 2/2006 | Ali et al. |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |
| 7,016,715 | B2 | 3/2006 | Stetson |
| 7,020,507 | B2 | 3/2006 | Scharf et al. |
| 7,024,233 | B2 | 4/2006 | Ali et al. |
| 7,024,235 | B2 | 4/2006 | Melker et al. |
| 7,025,728 | B2 | 4/2006 | Ito et al. |
| 7,027,849 | B2 | 4/2006 | Al-Ali et al. |
| 7,027,850 | B2 | 4/2006 | Wasserman |
| 7,039,449 | B2 | 5/2006 | Al-Ali |
| 7,043,289 | B2 | 5/2006 | Fine et al. |
| 7,047,055 | B2 | 5/2006 | Boaz et al. |
| 7,060,035 | B2 | 6/2006 | Wasserman et al. |
| 7,062,307 | B2 | 6/2006 | Norris et al. |
| 7,067,893 | B2 | 6/2006 | Mills et al. |
| 7,072,701 | B2 | 7/2006 | Chen et al. |
| 7,072,702 | B2 | 7/2006 | Edgar, Jr. et al. |
| 7,079,880 | B2 | 7/2006 | Stetson |
| 7,085,597 | B2 | 8/2006 | Fein et al. |
| 7,096,052 | B2 | 8/2006 | Mason et al. |
| 7,096,054 | B2 | 8/2006 | Abdul-Hafiz et al. |
| 7,107,088 | B2 | 9/2006 | Aceti |

| Patent/Pub No. | Date | Inventor(s) |
|---|---|---|
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,194,293 B2 | 3/2007 | Baker, Jr. |
| 7,198,778 B2 | 4/2007 | Achilefu et al. |
| 7,206,621 B2 | 4/2007 | Aoyagi et al. |
| 7,209,774 B2 | 4/2007 | Baker, Jr. |
| 7,215,984 B2 | 5/2007 | Diab et al. |
| 7,221,970 B2 | 5/2007 | Parke |
| 7,225,006 B2 | 5/2007 | Al-Ali et al. |
| 7,228,161 B2 | 6/2007 | Chin |
| 7,236,811 B2 | 6/2007 | Schmitt |
| 7,236,813 B2 | 6/2007 | Parker et al. |
| 7,239,902 B2 | 7/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,257,433 B2 | 8/2007 | Takamura et al. |
| 7,277,741 B2 | 10/2007 | Debreczeny et al. |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,328,053 B1 | 2/2008 | Diab et al. |
| 7,343,186 B2 | 3/2008 | Lamego et al. |
| 7,376,453 B1 | 5/2008 | Diab et al. |
| 7,383,070 B2 | 6/2008 | Diab et al. |
| 7,392,075 B2 | 6/2008 | Baker, Jr. |
| 7,430,444 B2 | 9/2008 | Pologe |
| 2001/0020122 A1 | 9/2001 | Steuer et al. |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0127777 A1 | 7/2004 | Richti et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147034 A1 | 7/2004 | Gore et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230106 A1 | 11/2004 | Schmitt et al. |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0014999 A1 | 1/2005 | Rahe-Meyer |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049470 A1 | 3/2005 | Terry |
| 2005/0049471 A1 | 3/2005 | Aceti |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |

| | | | | | | |
|---|---|---|---|---|---|---|
| 2005/0131286 A1 | 6/2005 | Parker et al. | DE | 69123448 | | 5/1997 |
| 2005/0168722 A1 | 8/2005 | Forstner et al. | DE | 19703220 | | 7/1997 |
| 2005/0192488 A1 | 9/2005 | Bryenton et al. | DE | 19640807 | A1 | 9/1997 |
| 2005/0192493 A1 | 9/2005 | Wuori | DE | 19647877 | A1 | 4/1998 |
| 2005/0197548 A1 | 9/2005 | Dietiker | DE | 19855521 | A1 | 6/2000 |
| 2005/0203357 A1 | 9/2005 | Debreczeny et al. | DE | 10030862 | | 1/2002 |
| 2005/0209517 A1 | 9/2005 | Diab et al. | DE | 20318882 UI | | 4/2004 |
| 2005/0228248 A1 | 10/2005 | Dietiker | EP | 0127947 | | 5/1984 |
| 2005/0250998 A1 | 11/2005 | Huiku | EP | 00194105 | B1 | 9/1986 |
| 2005/0256386 A1 | 11/2005 | Chan | EP | 00204459 | A3 | 12/1986 |
| 2005/0267346 A1 | 12/2005 | Faber et al. | EP | 0 262 779 | | 4/1988 |
| 2005/0272986 A1 | 12/2005 | Smith | EP | 0315040 | | 10/1988 |
| 2005/0277819 A1 | 12/2005 | Kiani et al. | EP | 0314331 | | 5/1989 |
| 2006/0020179 A1 | 1/2006 | Anderson | EP | 00352923 | A1 | 1/1990 |
| 2006/0020181 A1 | 1/2006 | Schmitt | EP | 0 360 977 | | 4/1990 |
| 2006/0030763 A1 | 2/2006 | Mannheimer et al. | EP | 00430340 | A3 | 6/1991 |
| 2006/0030764 A1 | 2/2006 | Porges | EP | 0435 500 | | 7/1991 |
| 2006/0052680 A1 | 3/2006 | Diab et al. | EP | 0572684 | | 5/1992 |
| 2006/0058594 A1 | 3/2006 | Ishizuka et al. | EP | 00497021 | A1 | 8/1992 |
| 2006/0074280 A1 | 4/2006 | Martis | EP | 0529412 | | 8/1992 |
| 2006/0084852 A1 | 4/2006 | Mason et al. | EP | 0531631 | | 9/1992 |
| 2006/0084864 A1 | 4/2006 | Schmitt et al. | EP | 0566354 | | 4/1993 |
| 2006/0084878 A1 | 4/2006 | Banet | EP | 0587009 | | 8/1993 |
| 2006/0089547 A1 | 4/2006 | Sarussi | EP | 00630203 | B1 | 9/1993 |
| 2006/0106294 A1 | 5/2006 | Maser et al. | EP | 0 572 684 | | 12/1993 |
| 2006/0122475 A1 | 6/2006 | Balberg et al. | EP | 00615723 | A1 | 9/1994 |
| 2006/0122517 A1 | 6/2006 | Banet | EP | 00702931 | A1 | 3/1996 |
| 2006/0129037 A1 | 6/2006 | Kaufman et al. | EP | 00724860 | A1 | 8/1996 |
| 2006/0129038 A1 | 6/2006 | Zelenchuk et al. | EP | 00793942 | A3 | 9/1997 |
| 2006/0129039 A1 | 6/2006 | Lindner | EP | 0 864 293 | | 9/1998 |
| 2006/0155198 A1 | 7/2006 | Schmid | EP | 01006863 | B1 | 10/1998 |
| 2006/0167350 A1 | 7/2006 | Monfre et al. | EP | 01006864 | B1 | 10/1998 |
| 2006/0173257 A1 | 8/2006 | Nagai | EP | 0875199 | | 11/1998 |
| 2006/0189861 A1 | 8/2006 | Chen et al. | EP | 00999214 | A1 | 12/1998 |
| 2006/0200014 A1 | 9/2006 | Fine et al. | EP | 0 898 933 | | 3/1999 |
| 2006/0200015 A1 | 9/2006 | Baker, Jr. | EP | 0898933 | | 3/1999 |
| 2006/0200016 A1 | 9/2006 | Diab et al. | EP | 1135184 | A1 | 6/2000 |
| 2006/0211925 A1* | 9/2006 | Lamego et al. ............... 600/310 | EP | 1184663 | A2 | 3/2002 |
| 2006/0217609 A1 | 9/2006 | Diab et al. | EP | 01332713 | A1 | 8/2003 |
| 2006/0247506 A1 | 11/2006 | Balberg et al. | EP | 01469773 | A1 | 8/2003 |
| 2006/0253016 A1 | 11/2006 | Baker, Jr. et al. | EP | 1502529 | | 7/2004 |
| 2006/0276696 A1 | 12/2006 | Schurman | EP | 1491135 | | 12/2004 |
| 2006/0287587 A1 | 12/2006 | Yarita | EP | 01491135 | A2 | 12/2004 |
| 2006/0287588 A1 | 12/2006 | Yarita | FR | 2685865 | | 1/1992 |
| 2007/0032710 A1 | 2/2007 | Raridan et al. | FR | 2710517 | | 4/1995 |
| 2007/0032712 A1 | 2/2007 | Raridan et al. | GB | 2 259 545 | | 3/1993 |
| 2007/0032715 A1 | 2/2007 | Eghbal et al. | JP | 63275325 | A | 11/1988 |
| 2007/0073126 A1 | 3/2007 | Raridan, Jr. | JP | 2013450 | | 1/1990 |
| 2007/0073127 A1 | 3/2007 | Kiani et al. | JP | 2111343 | A | 4/1990 |
| 2007/0106137 A1 | 5/2007 | Baker, Jr. et al. | JP | 02 191434 | | 7/1990 |
| 2007/0118027 A1 | 5/2007 | Baker, Jr. et al. | JP | 2237544 | A | 9/1990 |
| 2007/0129614 A1 | 6/2007 | Schmitt et al. | JP | 03 173536 | | 7/1991 |
| 2007/0129616 A1* | 6/2007 | Rantala ................ 600/323 | JP | 3170616 | | 7/1991 |
| 2007/0208242 A1 | 9/2007 | Baker, Jr. | JP | 3245042 | A | 10/1991 |
| 2007/0225581 A1 | 9/2007 | Diab et al. | JP | 4-40940 | | 2/1992 |
| 2007/0244376 A1 | 10/2007 | Wang | JP | 4174648 | A | 6/1992 |
| 2007/0249918 A1 | 10/2007 | Diab et al. | JP | 4191642 | A | 7/1992 |
| 2007/0282178 A1 | 12/2007 | Scholler et al. | JP | 4332536 | A | 11/1992 |
| 2007/0282183 A1 | 12/2007 | Scholler et al. | JP | 3124073 | B | 3/1993 |
| 2007/0291832 A1 | 12/2007 | Diab et al. | JP | 5049624 | A | 3/1993 |
| 2008/0004513 A1 | 1/2008 | Walker et al. | JP | 5049625 | A | 3/1993 |
| 2008/0004514 A1 | 1/2008 | Diab et al. | JP | 3115374 | B | 4/1993 |
| 2008/0009690 A1 | 1/2008 | Debreczeny et al. | JP | 05 200031 | | 8/1993 |
| 2008/0033266 A1 | 2/2008 | Diab et al. | JP | 2005/200031 | | 8/1993 |
| 2008/0036752 A1 | 2/2008 | Diab et al. | JP | 5212016 | A | 8/1993 |
| 2008/0045823 A1 | 2/2008 | Diab et al. | JP | 5-329163 | | 12/1993 |
| 2008/0081969 A1 | 4/2008 | Feldman et al. | JP | 06 014906 | | 1/1994 |
| 2008/0154104 A1 | 6/2008 | Lamego et al. | JP | 06014906 | | 1/1994 |
| 2008/0208019 A1 | 8/2008 | Nitzan | JP | 6016774 | B2 | 3/1994 |
| 2008/0255436 A1 | 10/2008 | Baker | JP | 3116255 | B | 4/1994 |
| | | | JP | 6029504 | U | 4/1994 |
| | FOREIGN PATENT DOCUMENTS | | JP | 6098881 | A | 4/1994 |
| DE | 3405444 | 8/1985 | JP | 06 154177 | | 6/1994 |
| DE | 3516338 | 11/1986 | JP | 6269430 | A | 9/1994 |
| DE | 37 03 458 | 8/1988 | JP | 6285048 | A | 10/1994 |
| DE | 3938759 | 5/1991 | JP | 7001273 | B2 | 1/1995 |
| DE | 4210102 A1 | 9/1993 | JP | 7124138 | A | 5/1995 |
| DE | 4423597 | 8/1995 | JP | 7136150 | A | 5/1995 |
| DE | 19632361 | 2/1997 | JP | 3116259 | B | 6/1995 |

| | | |
|---|---|---|
| JP | 3116260 B | 6/1995 |
| JP | 7155311 A | 6/1995 |
| JP | 7155313 A | 6/1995 |
| JP | 3238813 B2 | 7/1995 |
| JP | 7171139 A | 7/1995 |
| JP | 3134144 B | 9/1995 |
| JP | 7236625 A | 9/1995 |
| JP | 7246191 A | 9/1995 |
| JP | 8256996 A | 10/1996 |
| JP | 9192120 A | 7/1997 |
| JP | 10216113 A | 8/1998 |
| JP | 10216114 A | 8/1998 |
| JP | 10216115 A | 8/1998 |
| JP | 10337282 A | 12/1998 |
| JP | 11019074 A | 1/1999 |
| JP | 11155841 A | 6/1999 |
| JP | 11 188019 | 7/1999 |
| JP | 11-244266 | 9/1999 |
| JP | 11244268 A | 9/1999 |
| JP | 20107157 A | 4/2000 |
| JP | 20237170 A | 9/2000 |
| JP | 21245871 A | 9/2001 |
| JP | 22224088 A | 8/2002 |
| JP | 22282242 A | 10/2002 |
| JP | 23153881 A | 5/2003 |
| JP | 23153882 A | 5/2003 |
| JP | 23169791 A | 6/2003 |
| JP | 23194714 A | 7/2003 |
| JP | 23210438 A | 7/2003 |
| JP | 23275192 A | 9/2003 |
| JP | 23339678 A | 12/2003 |
| JP | 24008572 A | 1/2004 |
| JP | 2004 081427 A | 3/2004 |
| JP | 24089546 A | 3/2004 |
| JP | 24113353 A | 4/2004 |
| JP | 24135854 A | 5/2004 |
| JP | 24148069 A | 5/2004 |
| JP | 24148070 A | 5/2004 |
| JP | 24159810 A | 6/2004 |
| JP | 24166775 A | 6/2004 |
| JP | 24194908 A | 7/2004 |
| JP | 24202190 A | 7/2004 |
| JP | 24248819 A | 9/2004 |
| JP | 24248820 A | 9/2004 |
| JP | 24261364 A | 9/2004 |
| JP | 24290412 A | 10/2004 |
| JP | 24290544 A | 10/2004 |
| JP | 24290545 A | 10/2004 |
| JP | 24329406 A | 11/2004 |
| JP | 24329607 A | 11/2004 |
| JP | 24329928 A | 11/2004 |
| JP | 24337605 A | 12/2004 |
| JP | 24344367 A | 12/2004 |
| JP | 24351107 A | 12/2004 |
| JP | 25034472 A | 2/2005 |
| JP | 26075354 | 3/2005 |
| JP | 25095606 | 10/2005 |
| JP | 25278758 | 3/2006 |
| WO | WO 89/09566 A1 | 10/1989 |
| WO | WO 90/01293 A1 | 2/1990 |
| WO | WO 90/04352 | 5/1990 |
| WO | WO 91/01678 A1 | 2/1991 |
| WO | WO 91/11137 A1 | 8/1991 |
| WO | WO 92/00513 | 1/1992 |
| WO | WO 92/21281 | 12/1992 |
| WO | WO 92/21281 A1 | 12/1992 |
| WO | WO 93/09711 | 5/1993 |
| WO | WO 93/13706 A2 | 7/1993 |
| WO | WO 93/16629 A1 | 9/1993 |
| WO | WO 94/03102 A1 | 2/1994 |
| WO | WO 94/23643 | 10/1994 |
| WO | WO 94/23643 A1 | 10/1994 |
| WO | WO 95/02358 | 1/1995 |
| WO | WO 95/12349 A1 | 5/1995 |
| WO | WO 95/16970 | 6/1995 |
| WO | WO 95/19562 A | 7/1995 |
| WO | WO 96/13208 | 5/1996 |
| WO | WO 96/39927 A1 | 12/1996 |
| WO | WO 97/36536 | 10/1997 |
| WO | WO 97/36538 | 10/1997 |
| WO | WO 97/49330 A1 | 12/1997 |
| WO | WO 98/17174 A1 | 4/1998 |
| WO | WO 98/18382 | 5/1998 |
| WO | WO 98/34097 | 8/1998 |
| WO | WO 98/43071 A1 | 10/1998 |
| WO | WO 98/51212 A1 | 11/1998 |
| WO | WO 98/57577 A1 | 12/1998 |
| WO | WO 99/00053 | 1/1999 |
| WO | WO 99/32030 A1 | 7/1999 |
| WO | WO 99/47039 A1 | 9/1999 |
| WO | WO 99/63884 | 12/1999 |
| WO | WO 00/21438 A1 | 4/2000 |
| WO | WO 00/28888 A1 | 5/2000 |
| WO | WO 00/32262 A1 | 6/2000 |
| WO | WO 00/59374 A1 | 10/2000 |
| WO | WO 00/71025 A1 | 11/2000 |
| WO | WO 93/13706 A2 | 1/2001 |
| WO | WO 01/13790 | 3/2001 |
| WO | WO 01/16577 A1 | 3/2001 |
| WO | WO 01/17421 A1 | 3/2001 |
| WO | WO 01/47426 | 3/2001 |
| WO | WO 0116577 | 3/2001 |
| WO | WO 01/40776 A1 | 6/2001 |
| WO | WO 01/67946 | 9/2001 |
| WO | WO 01/76461 A1 | 10/2001 |
| WO | WO 02/14793 A3 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 A1 | 1/2003 |
| WO | WO 03/001180 | 1/2003 |
| WO | WO 03/009750 A3 | 2/2003 |
| WO | WO 03/010510 A | 2/2003 |
| WO | WO 03/011127 A1 | 2/2003 |
| WO | WO 03/020129 | 3/2003 |
| WO | WO 03/039326 A3 | 5/2003 |
| WO | WO 03/063697 | 8/2003 |
| WO | WO 03/063697 A1 | 8/2003 |
| WO | WO 03/073924 A1 | 9/2003 |
| WO | WO 2004/000114 | 12/2003 |
| WO | WO 2004/006748 A3 | 1/2004 |
| WO | WO 2004/069046 | 8/2004 |
| WO | WO 2004/075746 A2 | 9/2004 |
| WO | WO 2005/002434 | 1/2005 |
| WO | WO 2005/009221 A2 | 2/2005 |
| WO | WO 2005/010567 A2 | 2/2005 |
| WO | WO 2005/010568 A3 | 2/2005 |
| WO | WO 2005/020120 A2 | 3/2005 |
| WO | WO 2005/041765 A | 5/2005 |
| WO | WO 2005/065540 | 7/2005 |
| WO | WO2006097910 | 9/2006 |
| WO | WO 2006/104790 | 10/2006 |
| WO | WO2006124455 | 11/2006 |

OTHER PUBLICATIONS

U.S. Appl. No. 11/528,218, filed Sep. 27, 2006, Campbell, et al.
U.S. Appl. No. 11/529,024, filed Sep. 28, 2006, Agashe, et al.
U.S. Appl. No. 11/541,010, filed Sep. 29, 2006, Baker, Jr., et al.
Wheeler, Owen H., "Near Infrared Spectra of Organic Compounds," Department of Chemistry, College of Agriculture and Mechanic Arts, University of Puerto Rico (Mar. 1929).
Pace, Nello, et al., "Studies on Body Composition: III. The body water and chemically combined nitrogen content in relation to fat content," Naval Medical Research Institute, Bethesda, Maryland (Jan. 11, 1945).
Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).
Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.
Buijs, K., et al., "Near-Infrared Studies of the Structure of Water. I. Pure Water," *The Journal of Chemical Physics*, vol. 39, No. 8, pp. 2035-2041 (Oct. 15, 1963).
Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).
Goldstein, R., et al., "The Near-Infrared Absorption of Liquid Water at Temperatures Between 27 and 209° C.," *J. Quant. Spectrosc. Radiat. Transfer.*, vol. 4, pp. 441-451 (1964).
Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).
Houseman, R.A., et al., "The measurement of total body water in living pigs by deuterium oxide dilution and its relation to body composition," *Br. J. Nutr.*, vol. 30, pp. 149-156 (1973).
Krikorian, S. Edward, et al., "The identification and origin of N-H overtone and combination bands in the near-infrared spectra of simple primary and secondary amides," *Spectrochimica acta*, vol. 29A, pp. 1233-1246 (1973).
Lesser, G.T., et al., "Body water compartments with human aging using fat-free mass as the reference standard," *Am J. Physiol Regul Integr Comp Physiol.*, vol. 236, pp. 215-220 (1979).
Sheng, Hwai-Ping, et al., "A review of body composition studies with emphasis on total body water and fat," *The American Journal of Clinical Nutrition*, vol. 32., pp. 630-647 (Mar. 1979).
Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).
Fomon, Samuel J., et al., "Body composition of reference children from birth to age 10 years," The American Journal of clinical Nutrition, vol. 35, pp. 1169-1175, (May 1982).
Lanza, Elaine, "Determination of Moisture, Protein, Fat, and Calories in Raw Pork and Beef by near Infrared Spectroscopy," *Journal of Food Science*, vol. 48, pp. 471-474 (1983).
Shields, R. G., Jr., et al., "Efficacy of Deuterium Oxide to Estimate Body Composition of Growing Swine"; *Journal of Animal Science*, vol. 57, No. 1, pp. 66-73, (1983).
Wolfgang, Arneth, "Multivariate Infrared and near-infrared Spectroscopy: rapid analysis of protein, fat and water in meat," *Food Res and Data Analysis, Proc from IUoST Symp, Oslo, Norway*, pp. 239-251 (1983).
Cohn, S.H., et al., "Assessment of cellular mass and lean body mass by noninvasive nuclear techniques," *J. Lab Clin Med.*, vol. 105, pp. 305-311 (1985).
Hannon, John P., et al., "Splenic red cell sequestration and blood volume measurements in conscious pigs," *Am J. Physiol.*, vol. 248, pp. R293-R301 (1985).
Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).
Cox, Patrick, et al., "Variations in Lipids in Different Layers of Porcine Epidermis," *J. Invest Dermatol.*, vol. 87, pp. 741-744 (1986).
Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).
Hedberg, Chrisopher L., et al., "The Time Course of Lipid Biosynthesis in Pig Epidermis," *J. Invest Dermatol.*, vol. 91, pp. 169-174 (1988).
Hedberg, Christopher L., et al., "The nonpolar Lipids of Pig Epidermis," *J. Invest Dermatol.*, vol. 90, pp. 225-229 (1988).
Trapp, Scott A., et al., "An improved spectrophotometric bromide assay for the estimation of extracellular water volume," *Clinica Chimica Acta.*, vol. 181, pp. 207-212, (1989).
Bommannan, D., et al., "Examination of Stratum Corneum Barrier Function In Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.
Mak, Vivien H.W., et al., "Oleic Acid Concentration and Effect in Human Stratum Corneum: Non-Invasive determination by Attenuated Total Reflectance Infrared Spectroscopy in Vivo," *Journal of Controlled Release*, vol. 12, pp. 67-75 (1990).
Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.
Drummer, C., et al., "Effects of an acute saline infusion on fluid and electrolyte metabolism in humans," *Am J. Physiol.*, vol. 262, pp. F744-F754 (1992).
Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).
Schmitt et al., *Proc. SPIE*, "Measurement of blood hematocrit by dual-wavelength near-IP photoplethysmography," 1641:150-161 (1992).
Diaz-Carrillo, E., et al., "Near infrared calibrations for goat's milk components; protein, total casein, $\alpha_s$-$\beta$- and $k$-caseins, fat and lactose," *J. near Infrared Spectrosc.*, vol. 1, pp. 141-146 (1993).
Martin, K., "Direct Measurement of Moisture in Skin by NIR spectroscopy," *J. Soc. Cosmet. Chem.*, 44:249-261 (1993).
Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).
Thompson et al., "Can bioelectrical impedance be used to measure total body water in dialysis patients?", *Physiol. Meas.*, 14:455-461 (1993).
Bewig, Karen M., et al., "Discriminant Analysis of Vegetable Oils by Near-Infrared Reflectance Spectroscopy," *JAOCS*, vol. 71, No. 2, pp. 195-200 (Feb. 1994).
Kamishikiryo-Yamashita, Hiromi, et al, "Protein Content in Milk by Near-Infrared Spectroscopy," *Journal of Food Science*, vol. 59, No. 2, pp. 313-315 (1994).
Matcher, S. J., et al., "Absolute quantification of deoxyhaemoglobin concentration in tissue near infrared spectroscopy," *Phys. Med. Biol.*, vol. 39, pp. 1295-1312 (1994).
Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).
Steven, Alasdair C., et al., "Protein composition of cornified cell envelopes of epidermal keratinocytes," *Journal of Cell Science*, vol. 107, pp. 693-700 (1994).
Takeo, T. et al., "Skin Hydration State Estimation Using a Fiber-Optic Refractometer," *Applied Optics*, vol. 33, No. 19, Jul. 1994, p. 4267-72.
Warren, Joan L., et al., "The burden and Outcomes Associates with Dehydration among US Elderly, 1991," *American Journal of Public Health*, vol. 84, No. 8, pp. 1265-1269 (Aug. 1994).
Åneman, Anders, et al., "Splanchnic and Renal Sympathetic Activity in Relation to Hemodynamics During Isoflurane Administration in Pigs," *Anesth Analg.*, vol. 80, pp. 135-142, (1995).
Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).
Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).
Quiniou, N., et al., "Prediction of Tissular Body Composition from Protein and Lipid Deposition in Growing Pigs," *J. Anim. Sci.*, vol. 73, pp. 1567-1575, (1995).
Avis, N. J., et al.; "In vitro multifrequency electrical impedance measurements and modeling of the cervix in late pregnancy", *Physiological Measurement*, vol. 17, pp. A97-103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water," *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "PERSPECTIVES—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older Peoele to Maintain Skeletal Muscle," *Journal of Gerontology*, vol. 56A, No. 6, pp. M373-M380 (2001).

Divert, Victor E., "Body Thermal State Influence on Local Skin Thermosensitivity," *International Journal of Circumpolar Health*, vol. 60, pp. 305-311 (2001).

Du, Y., et al., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).

Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki, et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G., et al., "Unreliable use of standard muscle hydration value in obesity," *Am J. Physiol Endocrinal Metab.*, vol. 280, pp. E365-371, (2001).

Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogenous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. El-E7, (2001).

Watson, Walter, "Hydration of fat-free body mass: new physiological modeling approach," *Am J. PhysioL Endocrinol. Metab.*, Letters to the Editor, vol. 278, pp. E752-E753 (2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma Volume Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia," *Clin. Physiol. & Func. Im.*, vol. 22, pp. 197-201 (2002).

Meglinski, Igor V., et al., "Quantitative assessment of skin layers absorption and skin reflectance spectra simulation in the visible and near-infrared spectral regions," *PhysioL Meas.*, vol. 23, pp. 741-753, (2002).

Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr.*, vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional statusin simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of TRAUMA, Injury, Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27 pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C., et al., "Reducing Hydration=—Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24: 3383-390, 2003.

Rhodes, Andrew, et al., "Book Report—Haemodynamic monitoring in critically ill patients," *Critical Care*, vol. 8, p. 203 (2004).

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Ritz, Patrick, "Chronic Cellular Dehydration in the Aged Patient," Journal of Gerontology, vol. 56A, No. 6, pp. M349-M352 (2001).

Robinson, Martin P., et al., "A novel method of studying total body water content using a resonant cavity: experiments and numerical simulation," Phys. Med. Biol., vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U, et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *PhysioL Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.pdf (last accessed, Nov. 30, 2005).

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th — Nov. 2nd, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the $22^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the $22^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*, vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmogaphic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmogaphy and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Jornal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the*

26th Annual International conference of the IEEE EMBS, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Nogawa, Masamichi, et al.; "A New Hybrid Reflectance Optical Pulse Oximetry Sensor for Lower Oxygen Saturation Measurement and for Broader Clinical Application," SPIE, Biomedical Sensing, Imaging and Tracking technologies, Nov. 2, 1997; vol. 2976, pp. 78-87.

Odagiri, Y.; "Pulse Wave Measuring Device," Micromechatronics, vol. 42, No, 3, pp, 6-11 (published Sep. 1998) (Article in Japanese—contains English summary of article).

Garcia-Olmo, J., et al., "Advantages and disadvantages of multiple linear regression and partial least squares regression equatons for the prediction of fatty acids"Near Infrared Spectroscopy: Prceedings of the 9th International Conference on Near Infrared Spectroscopy, A.M.C. Davis and R. Giangiacomo Eds., NIR Publications; Chichester U.K. Feb. 10, 2000; pp. 253-258.

Wang, Zimian, et al., "Cellular-Level Body Composition Model—A New Approach to Studying Fat-free Mass Hydration," Annals of the New York Academy of Sciences, pp. 306-311 (May 2000).

Hamilton, Patrick S., et al.; "Effect of Adaptive Motion-Artifact Reduction on QRS Detection," Biomedical Instrumentation & Technology, pp. 197-202 (May-Jun. 2000).

Kim, J.M., et al.; "Signal Processing Using Fourier & Wavelet Transform for Pulse Oximetry," Lasers and Electro-Optics, 4th Pacific Rim Conference; pp. II-310-II-311 (2001).

Hayoz, J., et al.; "World's First Combined digital Pulse Oximetry Pulse Oximetry and Carbon Dioxide Tension Ear Sensor", Anesthesia & Analgesia 2002; 94: S103.

Huang, J., et al.; "Low Power Motion Tolerant Pulse Oximetry," Anesthesia & Analgesia 2002, 94: S103.

Lang, P., et al.; "Signal identification and Quality Indicator™ for Motion Resistant Pulse Oximetry," Anesthesia & Analgesia 2002; 94: S105.

Neumann, R., et al.; "Fourier Artifact suppression Technology Provides Reliable SpO2,," Anesthesia & Analgesia 2002; 94: S105.

Lee, C.M., et al.; "Reduction of Motion Artifacts from Photoplethysmographic Recordings Using a Wavelet Denoising Approach," IEEE, Biomedical Engineering, Oct. 2003; pp. 194-195.

\* cited by examiner

METHOD FOR DETECTION OF ABERRANT TISSUE SPECTRA

BACKGROUND OF THE INVENTION

1. Field of the Invention

The present invention relates generally to medical devices and, more particularly, to the determination of placement of a medical device.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. For example, to measure certain characteristics, a non-invasive sensor may be utilized that transmits electromagnetic radiation, such as light, through a patient's tissue and then photoelectrically detects the absorption and scattering of the transmitted or reflected light in such tissue. The physiological characteristics of interest may then be calculated based upon the amount of light absorbed and/or scattered or based upon changes in the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue. In this manner, the measured amount of light absorbed and/or scattered may then be used to estimate the amount of blood or tissue constituent in the tissue using various algorithms.

One technique for monitoring the physiological characteristics of a patient is commonly referred to as pulse oximetry, and devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsation supplying the tissue, and/or the rate of blood pulsations corresponding to each heart beat of a patient. Such physiological information allows doctors and other health care personnel to provide the best possible health care for their patients.

In processing a signal received by a pulse oximeter sensor, or any other non-invasive sensor utilizing similar data acquisition principles, the quality of the signal is typically dependent on the sensor making proper contact with the tissue. The sensor may be misplaced on the patient, or jostled or bumped, thereby affecting the contact of the sensor with the patient's tissue. In such instances, or in other circumstances where there may be poor contact between the sensor and the skin, light that otherwise might provide useful information may escape to the environment and never be detected or it may reach the light detection mechanism without passing through the patient's tissue, effectively providing no physiological information while reducing signal quality. Such lost or degraded information regarding the physiological characteristic, such as blood oxygen saturation, may result in an inaccurate indication of the patient's condition being provided to a health care provider.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for determining contact of a sensor with a patient's tissue that includes: emitting light at three or more wavelengths into a patient's tissue, wherein the three or more wavelengths includes a first wavelength that is not used to determine a physiological characteristic of the patient light; detecting the light; comparing the intensity of the detected light at the first wavelength to a threshold; and determining if the sensor is in contact with the patient's tissue based on the comparison.

There is also provided a method for correcting light shunting that includes: emitting light at three or more wavelengths into a patient's tissue, wherein the three or more wavelengths includes a first wavelength that is not used to determine a physiological characteristic of the patient light; detecting the light with at least one detector disposed on the sensor body; comparing the intensity of the detected light at the third wavelength to a threshold; and determining the amount of light shunting between the at least one emitter and the at least one detector based on the comparison.

A monitor is provided. The monitor includes: an I/O port configured to connect a sensor; and a processor configured to execute an algorithm configured to compare a wavelength of detected light to a threshold, wherein the wavelength is not used to determine a physiological characteristic of the patient, and an algorithm configured to determine if a sensor is in contact with the patient's tissue based on the comparison.

A sensor is provided. The sensor includes: one or more light emitting components configured to emit light at three or more wavelengths, wherein at least one of the wavelengths is not used to determine a physiological characteristic but is used to determine the sufficiency of contact between the sensor and the tissue of a patient; one or more light detecting components configured to detect the light emitted by the one or more light emitting components; and a sensor body upon which the one or more light emitting components and the one or more light detecting components are disposed A sensor assembly is provided. The sensor assembly includes: a sensor body; an emitter configured to emit light at three or more wavelengths into a patient's tissue; a detector configured to detect the light; and a monitor configured to execute an algorithm configured to compare a wavelength of detected light to a threshold, wherein the wavelength is not used to determine a physiological characteristic of the patient, and an algorithm configured to determine if a sensor is in contact with the patient's tissue based on the comparison.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a method for determining if a sensor, such as for use in pulse oximetry or other applications utilizing spectrophotometry, is in contact with a patient's tissue. Further, it is also desirable to provide a method for estimating the amount of light shunting in such a sensor and to use the estimated amount of light shunting to correct sensor measurements. In accordance with some aspects of the present technique, a patient sensor and monitor are provided that are configured to determine if the sensor is in suitable contact with the patient's tissue. If the sensor is not in suitable contact, a notification may be provided to a clinician or operator, allowing the clinician or operator to correct the lack of suitable contact.

Figure 1:
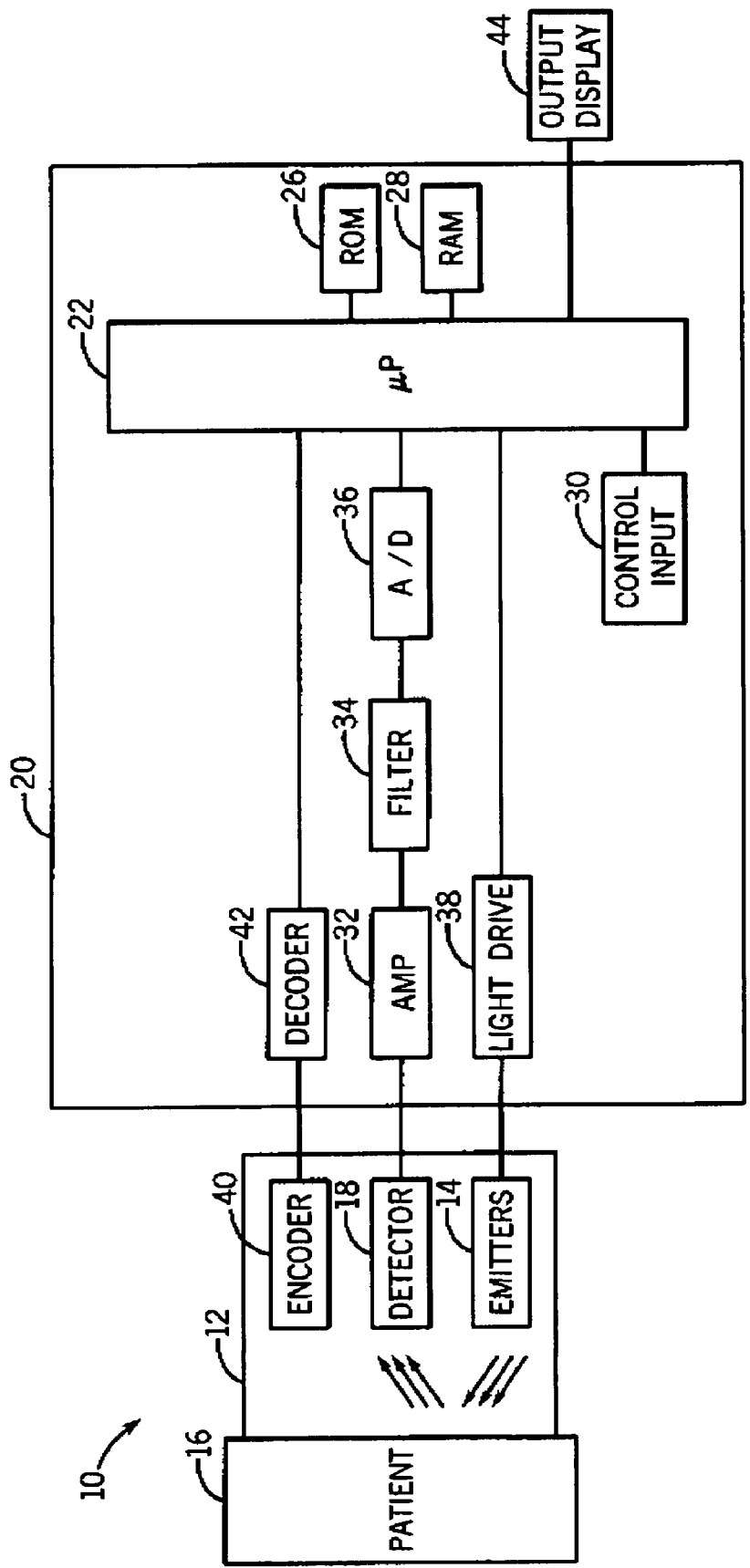
FIG. 1 illustrates a block diagram of a sensor and patient monitoring system in accordance with an exemplary embodiment of the present invention.

Prior to discussing the present technique in detail, it should be appreciated that exemplary acts of the present technique are typically implemented in a patient monitoring system including a sensor for attachment to a patient. For example, FIG. 1 illustrates a block diagram of a sensor and patient monitoring system 10 in accordance with an exemplary embodiment of the present approach. The system 10 is exemplary and an actual implementation may include more or fewer components as needed for a specific application for which the system 10 is to be used, such as for pulse oximetry applications. The system 10 includes a sensor assembly 12 for attachment to a patient 16. In an exemplary embodiment, the sensor assembly 12 includes an emitter 14 configured to emit electromagnetic radiation, such as light, into the tissue of the patient 16. The electromagnetic radiation is scattered and/or absorbed by the various constituents of the patient's blood and/or tissues. A photoelectric detector 18 in the sensor 12 is configured to detect the scattered and/or reflected light and to generate a corresponding electrical signal. In the depicted exemplary embodiment, the electrical signal is provided to a spectrophotometric monitor 20, such as a pulse oximetry or multi-parameter monitor, such as those available from Nellcor Puritan Bennett, Inc.

In the depicted embodiment, the spectrophotometric device or patient monitor 20 has a microprocessor 22 which calculates various patient parameters, characteristics, and/or other metrics using algorithms programmed into the monitor 20. The microprocessor 22 is connected to other component parts of the monitor 20, such as a ROM 26, a RAM 28, and control inputs 30. In certain embodiments, the ROM 26 holds the algorithms used to compute the patient parameters, characteristics, and/or metrics. The RAM 28 stores the values detected by the detector 18 for use in the algorithms.

In some embodiments, one or more control inputs 30 allow a user to interface with the spectrophotometric monitor 20. Patient data may be entered, such as gender, weight, age and medical history data. This information may be used to validate the baseline measurements or to assist in the understanding of anomalous readings. The control inputs 30 may include soft keys, dedicated function keys, keyboard, and/or keypad type interfaces for providing parameters, data or instructions to the monitor 20. In certain embodiments, the control input 30 may also include speech or tone recognition or other audio command input type devices.

Signals are passed from the sensor 12 to the spectrophotometric monitor 20 for processing. In one embodiment, the signals are amplified and filtered by amplifier 32 and filter 34, respectively, before being converted to digital signals by an analog-to-digital converter 36. The signals may then be used to determine the patient parameters, characteristics, and/or metrics and/or stored in RAM 28.

A light drive unit 38 in the spectrophotometric monitor 20 controls the timing of the emitters 14. While the emitters 14 are manufactured to operate at one or more certain wavelengths, variances in the wavelengths actually emitted may occur which may result in inaccurate readings. To help avoid inaccurate readings, an encoder 40 and decoder 42 may be used to calibrate the spectrophotometric monitor 20 to the actual wavelengths emitted by the emitters 14. The encoder 40 may be a resistor, for example, whose value corresponds to coefficients stored in the spectrophotometric device 20. The coefficients may then be used in the algorithms. Alternatively, the encoder 40 may also be a memory device, such as an EPROM, that stores information, such as the coefficients themselves. Once the coefficients are determined by the spectrophotometric monitor 20, they are inserted into the algorithms in order to calibrate the system 10.

The spectrophotometric monitor 20 may be configured to display the calculated values, such as blood oxygen saturation, tissue hydration, and so forth, on display 44. The display 44 may show the calculated values numerically and/or as a waveform over time. Additionally, any notifications or alerts prompted by abnormal measurements or calculated values or by poor contact between the sensor and the patient's tissue, as discussed below, may be displayed on the display 44.

Figure 2:
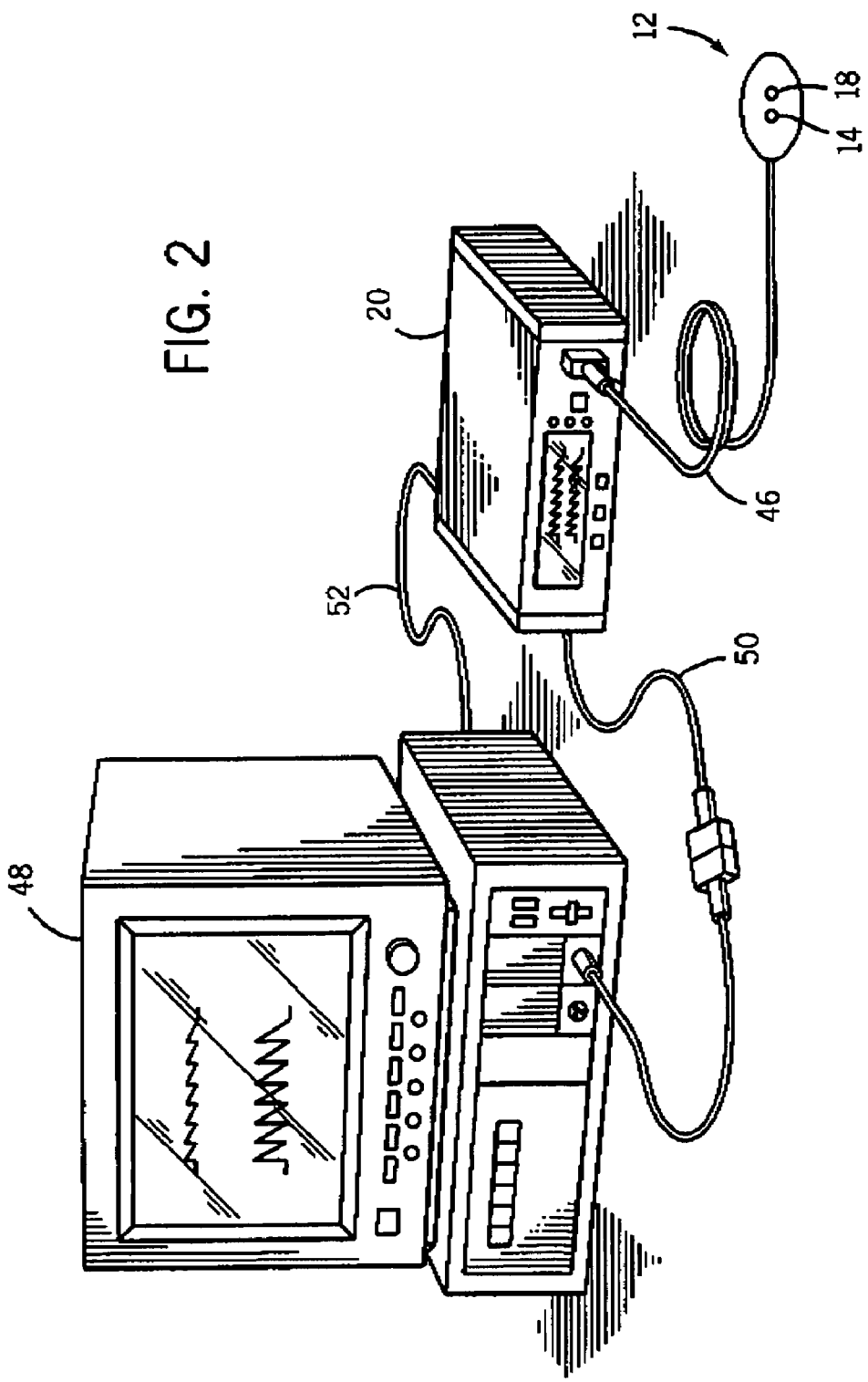
FIG. 2 illustrates a patient monitoring system coupled to a multi-parameter patient monitor and a reflectance-type forehead sensor, in accordance with aspects of the present technique.

Referring now to FIG. 2, the sensor 12, which may be a pulse oximetry or other spectrophotometric sensor such as a spectrophotometric sensor available from Nellcor Puritan Bennett, Inc., is shown as an exemplary reflectance-type forehead sensor for use in conjunction with a patient monitor 20. In the depicted embodiment, a sensor cable 46 connects the sensor 12 to the patient monitor 20. As will be appreciated by those of ordinary skill in the art, the sensor 12 and/or the sensor cable 46 may include or incorporate one or more integrated circuit devices or electrical devices, such as a memory, processor chip, or resistor, that may facilitate or enhance communication between the sensor 12 and the patient monitor 20. For example, as described above, the sensor 12 or the cable 46 may include an encoder 40 for storing values or identifying information which may be used by the monitor 20 in operation. Likewise the sensor cable 46 may be an adaptor cable, with or without an integrated circuit or electrical device, for facilitating communication between the sensor 12 and various types of monitors, including older or newer versions of the patient monitor 20 or other physiological monitors. The cable 46 may be permanently coupled to the sensor 12, or it may be removably coupled to the sensor 12—the latter alternative being more useful and cost efficient in situations where the sensor 12 is disposable.

As will be appreciated by those of ordinary skill in the art, the sensor cable 46 is typically used to transmit control or timing signals from the monitor 20 to the sensor 12 and/or to transmit acquired data from the sensor 12 to the monitor 20. In other embodiments, the sensor 12 and the patient monitor 20 may communicate via wireless means, such as using radio, infrared, or optical signals. In such embodiments, a transmission device (not shown) may be connected to the sensor 12 to facilitate wireless transmission between the sensor 12 and the patient monitor 20.

In one embodiment, the patient monitor 20 may be a suitable pulse oximeter, such as those available from Nellcor Puritan Bennett Inc. In other embodiments, the patient monitor 20 may be a monitor suitable for measuring tissue hydration, glucose levels, or other blood or tissue related metrics, using spectrophotometric or other techniques. Furthermore, the monitor 20 may be a multi-purpose monitor suitable for performing pulse oximetry and measurement of tissue hydration, or other combinations of physiological and/or biochemical monitoring processes, using data acquired via the sensor 12. Furthermore, to supplement the monitoring functions provided by the monitor 20, the monitor 20 may be coupled to a multi-parameter patient monitor 48 via a cable 50 connected to a sensor input port and/or via a cable 52 connected to a digital communication port.

Figure 3:
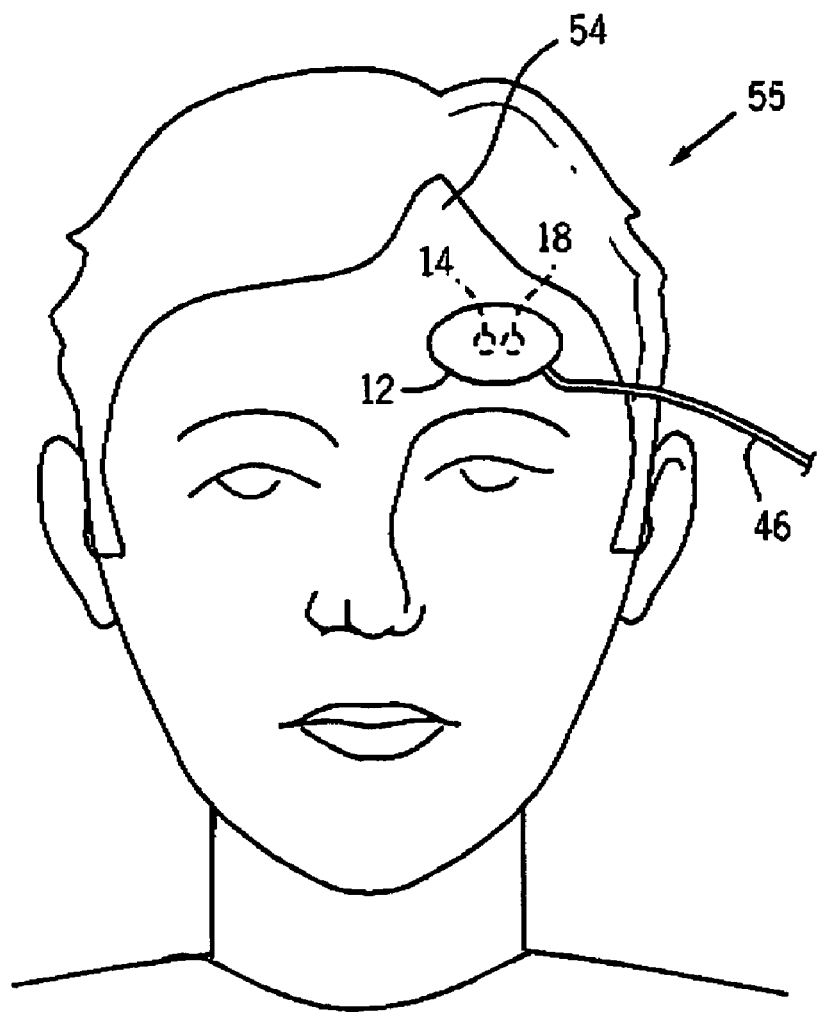
FIG. 3 illustrates the reflectance-type forehead patient sensor of FIG. 2 in use on a patient's forehead, in accordance with aspects of the present technique.

The exemplary sensor 12 depicted in FIGS. 1-3 includes an emitter 14 and a detector 18, as discussed with regard to FIG. 1, which may be of any suitable type. For example, the emitter 14 may be one or more light emitting diodes adapted to transmit one or more wavelengths of light, such as in the red to infrared range, and the detector 18 may be one or more photodetectors, such as a silicon photodiode package, selected to receive light in the range emitted from the emitter 14. The type and number of detectors 24 present in the sensor 12 may depend on how many and what wavelengths are emitted by the emitter 14.

The exemplary sensor 12 described with regard to FIGS. 1-3 is depicted as a reflectance-type sensor for use in pulse oximetry or other spectrophotometric applications, though in some embodiments of the present technique it may instead be configured for use as a transmission-type sensor. Transmission-type sensors include an emitter 14 and detector 18 that are typically placed on opposing sides of the sensor site. During operation, the emitter shines one or more wavelengths of light through the patient's fingertip or other tissue, and the light received by the detector is processed to determine the desired physiological characteristics of the patient.

Reflectance-type sensors include an emitter 14 and detector 18 that are typically placed on the same side of the sensor site, as generally depicted with regard to FIGS. 1-3. During operation, the emitter shines one or more wavelengths of light into the patient's tissue. A certain amount of the light is eventually reflected back toward the tissue surface where it is detected by the detector and processed to determine the desired physiological characteristics of the patient. For simplicity, the exemplary embodiment of the sensor 12 described herein is adapted for use as a reflectance-type sensor. As will be appreciated by those of ordinary skill in the art, however, such discussion is merely exemplary and is not intended to limit the scope of the present technique.

For pulse oximetry applications using either transmission or reflectance type sensors, the oxygen saturation of the patient's arterial blood may be determined using two or more wavelengths of light, most commonly red and near infrared wavelengths. Similarly, in other applications, tissue hydration (or other body fluid related metric) or a concentration of one or more biochemical components in an aqueous environment may be measured using two or more wavelengths of light, most commonly near infrared wavelengths between about 1,000 nanometers to about 2,500 nanometers. It should be understood that, as used herein, the term "light" may refer to one or more of radio wave, millimeter wave, microwave, infrared, visible, ultraviolet, or even X-ray electromagnetic radiation, and may also include any wavelength within the radio wave, millimeter wave, microwave, infrared, visible, ultraviolet, or X-ray spectra.

Pulse oximetry and other spectrophotometric sensors, whether transmission-type or reflectance-type, are typically placed on a patient in a location conducive to measurement of the desired physiological parameters. Common pulse oximetry sensor sites include a patient's fingertips, toes, forehead, or earlobes. Regardless of the placement of the sensor 12, the reliability of the spectrophotometric measurement is related to the accurate detection of transmitted or reflected light that has passed through the patient's tissue and has not been inappropriately supplemented by outside light sources or modulated by subdermal anatomic structures. Such inappropriate supplementation and/or modulation of the light emitted by the sensor 12 can cause variability in the resulting spectrophotometric measurements. Therefore, to ensure accurate detection of the transmitted or reflected light, the sensor 12 should remain in contact with the patient's tissue. Failure to do so can result in inaccurate measurement of the desired physiological characteristics.

Another factor that may affect the sensor's reliability is the occurrence of light shunting. As discussed above, the accurate detection of transmitted or reflected light is related to the reliability of the pulse oximetry measurement. Light shunting occurs when light emitted from the emitter 14 in the sensor 12 arrives at the detector 18 without first having traveled through the patient's tissue. The light shunting may cause measurement variations that do not relate to the amount of blood or tissue constituent and, therefore, may lead to inaccurate measurements. Light shunting may be minimized by ensuring adequate contact between the sensor 12 and the patient's tissue. However, in the event light shunting occurs, the effects of light shunting may be corrected using the techniques described herein.

Turning now to FIG. 3, the exemplary reflectance-type sensor 12 is shown fitted to the forehead 54 of a patient 55. Further, as discussed above, the sensor 12 is connected to the monitor 20 by a sensor cable 46. The physical connection of the sensor 12 to the monitor 20 by the sensor cable 46 and the mechanism of attachment to the forehead 54 (such as adhesives, bandages, and so forth) may cause or allow the sensor 12 to be moved relative to the measurement site, i.e., forehead 54, due to incidental motion of the patient 55 or of nearby medical personnel. Additionally, the sensor 12 may be mistakenly removed by the patient 55 or medical personnel. The present technique provides exemplary acts to determine if the sensor 12 is in suitable contact with the patient's tissue, such as the patient's forehead 54.

As noted above, for spectrophotometric applications measuring blood or tissue constituent levels, contact between the sensor 12 and the intended tissue bed is important. In one embodiment of the present technique, the presence of water, which is an abundant component of virtually all tissue beds to which an optical sensor is typically applied, is used to determine whether the sensor 12 is in suitable contact with the tissue. In such an embodiment, the emitter 14 emits light at a wavelength at which water is generally opaque, so that light emitted at the wavelength is generally not reflected through the tissue when the sensor is in suitable contact with the tissue. Typically the light emitted at the water-opaque wavelength is in addition to the wavelengths employed for measuring the physiological characteristic of interest, such as blood oxygen saturation.

In such an embodiment, suitable contact between the sensor 12 and the tissue may be indicated by the general absence of light at the water-opaque wavelength at the detector 18 due to the absorption of light at that wavelength by the tissue. Conversely, insufficient contact between the sensor 12 and the tissue may be indicated by an unexpectedly high measurement of light at the water-opaque wavelength at the detector 18. For example, in a situation where the sensor 12 is in poor contact with the tissue, an unexpectedly high measurement of light at the water-opaque wavelength may be observed at the detector 18 (such as due to reflection of the light off of the tissue surface or multiple reflections between the tissue surface and the sensor interior) compared to a situation where the sensor 12 is in good contact with the tissue.

A typical water absorption band used in an exemplary sensor embodiment is between about 1,200 nanometers to about 1,600 nanometers, but additional wavelengths and absorption bands may also be used. The wavelengths of the emitted light may be selected based upon the absorption bands of any desired blood or tissue constituents. Further, the absorption band, and therefore the choice of light sources in the emitter 14, may be chosen based upon the expected or average optical path length, i.e. the distance between the emitter 14 and the detector 18, when the sensor 12 is positioned on a patient.

For example, an emitter 14 may emit light at a water-opaque wavelength between about 1,400 nanometers to about 1,600 nanometers in an implementation where the emitter 14 and detector 18 are separated by about 2.5 mm to about 4.5 mm. In other embodiments, the light emitted at the additional water-opaque wavelength may be in the wavelength range between about 1,200 nanometers to about 1,400 nanometers or between about 1,870 nanometers to about 2,000 nanometers. For example, in implementations where the emitter 14 and detector 18 are about 10 mm apart from one another (as is typically observed where transmission-type oximetry sensors are employed on a finger), the additional water-opaque wavelength may be between about 1,200 nanometers to about 1,400 nanometers. Light in this wavelength range is more penetrating of water and is, therefore, more likely to be detectable across the greater optical path length.

As will be appreciated by those of ordinary skill in the art, selection of a suitable wavelength for the additional wavelength may be based upon the desired amount of detectable signal at the detector 18, the tissue constituent (such as water) which is to be generally opaque to the light, and/or the expected optical path length. Longer, less penetrating wavelengths may be chosen based on a combination of the opacity of water, the optically dominant blood or tissue component, and the expected optical path length. For example, a longer wavelength may be used when less penetration of the tissue at the sensor site is desired, such as in embodiments where a reflectance-type sensor 12 is used on the forehead such that the emitter and detector have a relatively short optical path length.

The preceding examples relate to the use of water as the tissue constituent used to assess sensor placement. However, one of ordinary skill in the art will recognize that water is only one example and that virtually any tissue constituent may be utilized if the constituent is present in sufficient quantities at the sensor site so as to absorb light and if a suitable wavelength can be identified for which the constituent is substantially opaque. For example, hemoglobin and/or myoglobin may be satisfactory tissue constituents for use in accordance with the present technique as they are present throughout the body and have the desired optical traits. In this example, a wavelength in the range of about 500 nm to about 600 nm, where hemoglobin or myoglobin may be the dominant optical absorbers, may be used to verify that a sensor 12 is in contact with tissue containing adequate quantities of these analytes.

The preceding discussion has related examples of tissue constituents that may be employed in accordance with the present technique and exemplary wavelengths that may be absorbed by these constituents. The use of these wavelengths in assessing sensor contact is now discussed. For example, in one implementation water is the tissue constituent of interest and light is emitted by the sensor 12 at a water-opaque wavelength of about 1,480 nanometers. In this implementation, when the sensor 12 is in suitable contact with the patient 16, the amount of light measured by the detector 18 at this water-opaque wavelength is less than or equal to about two percent of a reference intensity measurement taken using a water-free substance at the same light wavelength. In other words, in such an implementation, the reference intensity measurement at the same wavelength in the absence of water is fifty times the intensity of the light detected when the sensor 12 is in sufficient contact with the tissue. Therefore, in such an implementation with suitable sensor-tissue contact, the water within the intervening tissue between the emitter 14 and detector 18 absorbed approximately ninety-eight percent or more of the emitted light having a wavelength of 1,480 nanometers relative to a comparable water-free volume. However, for sensor placements where the sensor 12 is not in good contact with the tissue, the amount of light at 1,480 nanometers reaching the detector 18 may be roughly ten times greater than the amount of light reaching the detector when there is sufficient sensor contact. In other words, the intensity of light at the water-opaque wavelength is 20% of the reference intensity of light at the same wavelength measured in a comparable water-free volume.

Thus, in such an implementation, observation of an unexpectedly high amount of light at a water-opaque frequency, such as 1,480 nanometers, may be used to determine the sufficiency of sensor-tissue contact. For example, the amount of light detected by the detector 18 at the water-opaque wavelength (assuming water is the tissue constituent being assessed) may be compared to a threshold value to determine sensor contact sufficiency. For example, such a threshold may be empirically set according to the observations described above, i.e., as a ratio or multiple of the intensity of the detected light at the water-opaque wavelength to a reference intensity measurement taken from a water-free substance at the same water-opaque wavelength. In one such example, a threshold is set such that light detected at the water-opaque wavelength that is greater than or equal to 20% of a reference intensity measurement at that same wavelength may indicate that the sensor 12 is not in good contact with the tissue of the patient 16. Other ratios, such as 30%, 40%, 50%, and so forth, may be employed. As will be appreciated, the selection of the threshold, whether selected empirically or as a fraction or ratio of a reference intensity measurement, will generally determine the sensitivity of the system in assessing the sufficiency of sensor placement and may be selected based on the desired sensitivity. Any fraction or ratio up to or including 100% of a reference intensity measurement may be used depending on the desired sensitivity of the system. Other factors that may be considered in establishing the threshold include the risk tolerance for false-positive and false-negative results and/or the time sensitivity between when a sensor 12 begins to lose sufficient contact and when a notification is provided.

As will be appreciated, thresholds based on the reference intensity measurements taken using a water-free substance may be generated before and/or during the monitoring session. Alternatively, the thresholds may be stored in a memory component, such as encoder 40, ROM 26, and/or RAM 28, of the sensor 12, the monitor 20 or 48, and/or the cable 46. In such an implementation, the thresholds may be stored in the memory component at the time of manufacture of the respective component or after manufacture, such as at the time of first use of the sensor 12. In addition, the thresholds stored in the memory component may be updated, if desired, at subsequent fixed time or usage intervals.

In another embodiment, the threshold may not be determined from an intensity measurement of a water-free substance at the same water-opaque wavelength as described above. For example, the amount of light at a water-opaque wavelength reaching the detector 18 may instead be compared to the amount of light at a different reference wavelength reaching the detector 18. In such an implementation, the reference wavelength may be less opaque, i.e., more penetrating, relative to water and may be measured concurrently or alternatingly on the same tissue as the water-opaque wavelength of light. In one such embodiment, the reference wavelength may be one of the wavelengths employed in measurement of physiological characteristics using the sensor 12, such as a red or near infrared wavelength. In this manner, the ratio of the intensity of the detected light at the water-opaque wavelength relative to the intensity of the detected light at the reference wavelength provides an indication of the quality of sensor contact with the patient's tissue. For example, if the sensor 12 is in good contact with the patient's tissue, the intensity of the detected light at the water-opaque wavelength may only be two percent of the intensity of the detected light at a red or near infrared wavelength that has been absorbed and reflected back to the detector 18. If, however, the sensor is not in good contact with the patient's tissue, most of the light at the water-opaque wavelength will not be absorbed by the water in the patient's tissue and may instead be reflected to the detector 18. In this case the ratio of the intensity of the detected light at the water-opaque wavelength to the intensity of the detected light at the reference red or near infrared wavelengths will be much greater.

As a result, an amount of light detected at the water-opaque wavelength that is too high relative to the light detected at a reference visible or infrared wavelength may be used as a threshold. For example, if the amount of light detected at the water-opaque wavelength is expected (such as due to empirical analysis or experience) to be 5% of the light detected at a reference wavelength, a threshold may be established at the expected ratio, i.e., 5%, or at some value greater than the expected ratio, such as 8%, 10%, 15%, and so forth. In this manner, thresholds based on a reference wavelength may be established that take time sensitivity and/or risk sensitivity to false-negative and false-positive readings into account. As will be appreciated, though use of a single visible or infrared reference wavelength has been discussed for simplicity, more than one reference wavelength may be employed in assessing sensor contact sufficiency.

For example, in a pulse oximetry context, two additional wavelengths of light may be used in assessing the physiological characteristics of interest. In such an implementation, one or both of the physiological wavelengths may be employed in assessing sensor contact. For example, a separate threshold may be employed relative to each physiological wavelength or a single threshold may be employed based on the aggregate light intensity for the combined physiological wavelengths. As will be appreciated, in contexts where multiple reference wavelengths are employed, the comparisons, and related determinations of sensor contact sufficiency, may be independent of one another, i.e., the light detected at the water-opaque wavelength may be separately and independently compared to each reference wavelength Alternatively, the comparisons may be combined, i.e., both thresholds must be exceeded to generate an indication that the sensor contact is insufficient, or may be hierarchical in nature, i.e., the threshold associated with the second reference wavelength is checked only after the threshold associated with the first reference wavelength is exceeded. While the preceding examples have related to the use of water as the tissue constituent and of corresponding water-opaque wavelengths, as noted previously, other constituents such as hemoglobin or myoglobin may also be employed along with suitable wavelengths of light that are absorbed by the selected tissue constituent.

Figure 4:
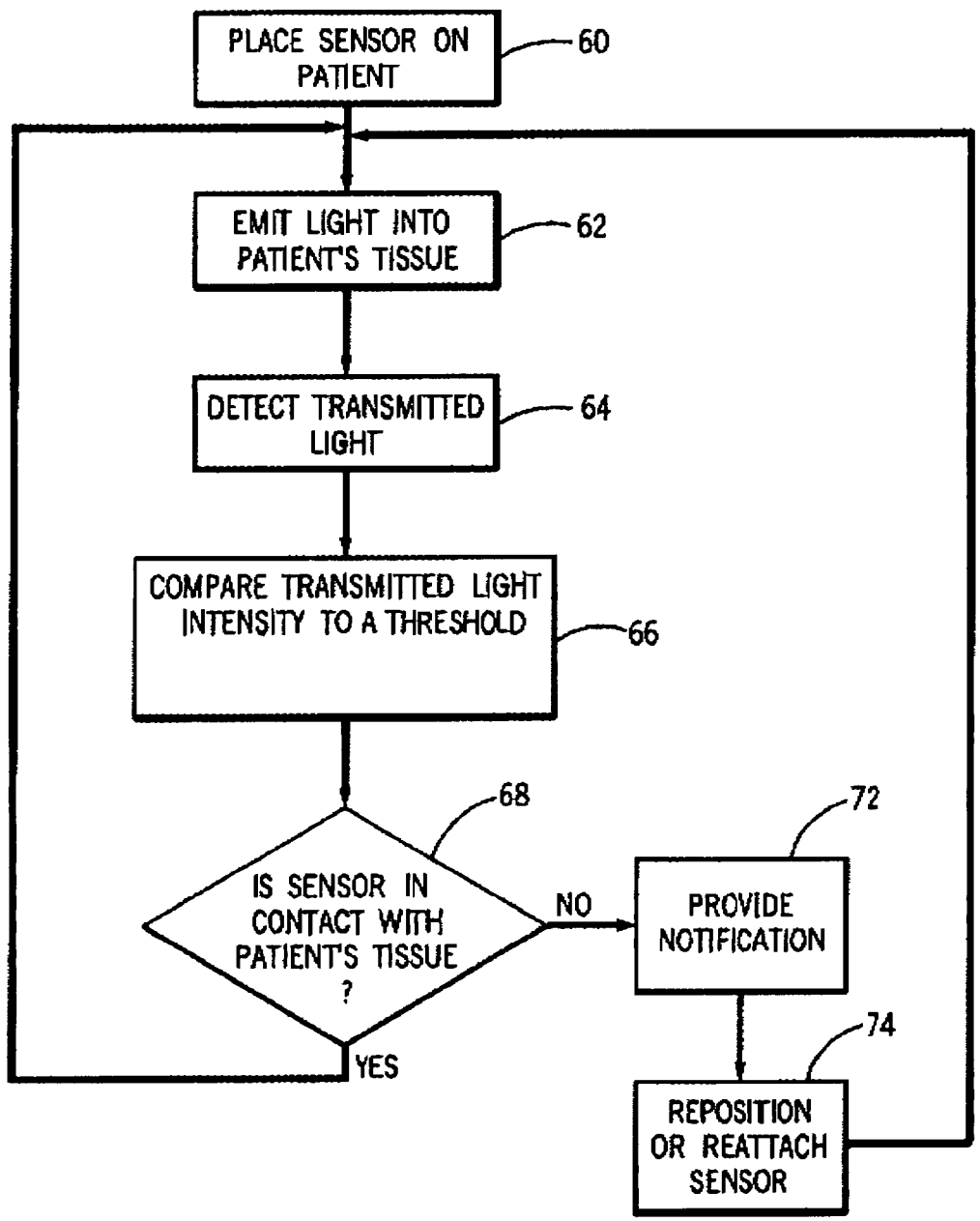
FIG. 4 is a flowchart depicting exemplary actions for determining contact of a sensor with a patient's tissue, in accordance with the present technique.

With the preceding discussion in mind and referring now to FIG. 4, exemplary acts for determining contact between a sensor 12 and a patient's tissue in accordance with the present technique are depicted. The acts described in FIG. 4 may be performed with any configuration of sensor, i.e., transmission or reflectance sensors, and with different types of spectrophotometric monitoring systems, such as systems for measuring blood oxygen saturation or tissue hydration. For simplicity, however, the actions described with relation to FIG. 4 are discussed with reference to an exemplary pulse oximetry implementation.

Turning now to FIG. 4, the sensor 12 is placed on the patient (block 60), such as attached onto a patient's forehead 54. The emitter 14 emits light into the patient's tissue (block 62). In addition to the red and near infrared wavelengths used for pulse oximetry, a third wavelength of light is also emitted which is different from those used in deriving pulse oximetry measurements. As discussed above, the third wavelength of light is absorbed by various blood or tissue constituents, such as water, myoglobin, or hemoglobin. In one pulse oximetry embodiment, the third wavelength is in the range of about 1,200 nanometers to about 1,400 nanometers, i.e. a water-opaque wavelength. The reflected light from the emitter is received by the detector (block 64) after absorption by blood and tissue constituents. The intensity of the light detected at the third wavelength is compared to a reference intensity measurement or wavelength (block 66), as described above. Based upon the comparison between the intensity of the reflected light of the third wavelength and the reference, the quality of the contact between the sensor and the patient's tissue may be determined (block 68).

If the ratio of the intensity of the reflected light to the reference intensity is below a threshold value, then the sensor is determined to be in contact with the patient's tissue. For example, in one embodiment, the intensity of the reflected light at the exemplary wavelength should be approximately two percent or less of the reference intensity when the sensor 12 is in good contact with the patient, i.e., the threshold value is two percent. Conversely, in this example, if the ratio of the intensity of the reflected light to the reference intensity is above the threshold value, the sensor is determined to not be in adequate contact with the patient's tissue. For example, in various respective embodiments, if the intensity of the reflected light at the exemplary water-opaque wavelength is more than 20%, 40%, or 50% greater than the intensity of the reflected light at sufficient sensor contact, the sensor 12 is determined to have poor contact with the patient's tissue.

If the sensor is determined to be in good contact with the patient's tissue, monitoring continues and no notification (or a positive indication of suitable contact) is provided to a technician or clinician. If the sensor is determined not to be in good contact with the patient's tissue, a notification is provided to the technician or clinician (block 72). The notification may be audio, visual, or both, and may be displayed on the sensor 12, patient monitor 20, or multi-parameter monitor 48. Following this notification, the operator may attempt to reattach or reposition the sensor (block 74) to achieve suitable sensor contact. Once the sensor is repositioned or reattached, monitoring may be resumed.

Figure 5:
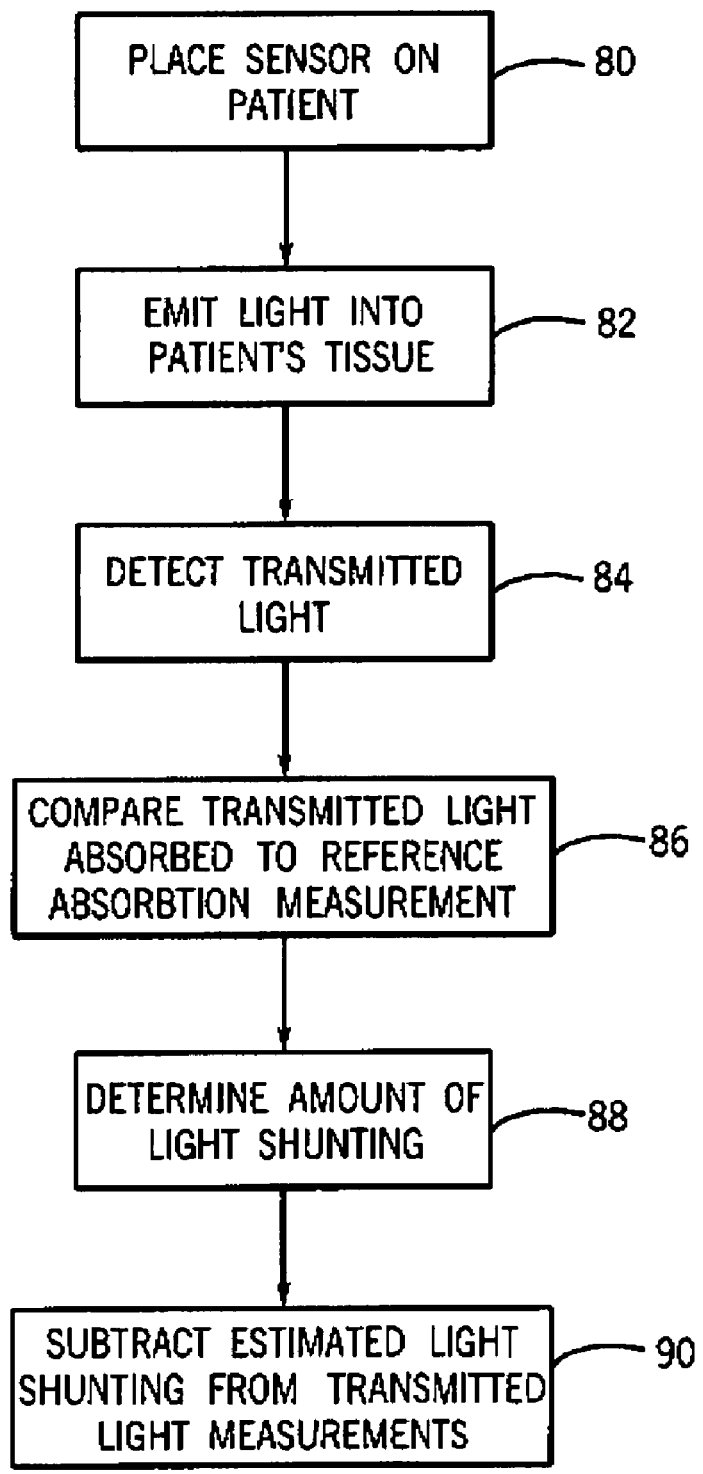
FIG. 5 is a flowchart depicting exemplary actions for correcting light shunting in a sensor, in accordance with the present technique.

In other embodiments of the present technique, a measure of light shunting may be determined instead of or in addition to an indication of sensor contact. For example, turning to FIG. 5, exemplary acts for determining the amount of light shunting in accordance with the present technique are depicted. The acts described in FIG. 5 may be performed in any configuration of the sensor and monitor system, including transmission and reflectance sensors and measurement of different physiological characteristics such as blood oxygen saturation or tissue hydration. For the purpose of illustration, an exemplary pulse oximetry implementation will be described, though other monitoring applications are also encompassed.

The sensor is first placed on the patient (block 80), such as attached onto a patient's forehead 54 using a suitable sensor 12 as described above. The emitter 14 emits light into the patient's tissue (block 82). In addition to the red and near infrared wavelengths used for pulse oximetry, a third wavelength of light is also emitted which is different from those used in deriving pulse oximetry measurements. As discussed above, in one embodiment, the third wavelength is in the range of about 1,200 nanometers to about 1,400 nanometers, i.e. a water-opaque wavelength. The reflected light of the third wavelength is received by the detector (block 84) after absorption by blood and tissue constituents. The percentage of reflected light of the third wavelength received at the detector 18 is compared to a reference value (block 86). In one embodiment, the reference value is the intensity of reflected light absorbed under normal conditions, i.e. with no light shunting. The reference value may be the intensity of reflected light at the same wavelength in the absence of shunting or the reference value may be taken at a different wavelength with a known absorption relationship to the third wavelength. From this comparison, the amount of light shunting is determined (block 88).

For example, the observed reflected light at the third wavelength may be approximately 99.2% absorbed and the normal absorption as determined by the reference absorption measurement may be approximately 99.8%. The difference between the two percentages corresponds to the amount of light shunting occurring during operation of the sensor under the present conditions. The estimated amount of light shunting can be subtracted or otherwise compensated for in the reflected light measurements at other wavelengths (block 90), such as the reflected light measurements received in the red and near infrared wavelengths used in a pulse oximetry sensor. For example, the light shunting at the exemplary water-opaque wavelength may be proportional to the light shunting at the visible or infrared wavelengths in a one-to one relationship or in some other empirically determined scaled relationship. The desired physiological characteristics, such as blood oxygen saturation, can be determined from the reflected light measurement at the other wavelengths emitted by the sensor corrected for the amount of light shunting observed at the third wavelength. Those skilled in the art will appreciate that subtracting or otherwise compensating for shunted light at these other wavelengths may involve rescaling the measured shunt at the third wavelength, based on factors such as emitter or detector efficiency or the optical reflective properties of skin or of the sensor interior.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission-type sensors for use in pulse oximetry, but also to reflectance-type sensors and other sensor designs as well. Likewise, the present techniques are not limited to use on fingers and toes but may also be applied to placement on other body parts such as in embodiments configured for use on the ears, nose, or forehead.

What is claimed is:

1. A method for determining contact of a sensor with a patient's tissue, comprising:
    emitting light at three or more wavelengths into a patient's tissue, wherein the three or more wavelengths includes a first wavelength that is not used to determine a physiological characteristic of the patient;
    detecting the light;
    comparing the intensity of the detected light at the first wavelength to a threshold;
    determining if the sensor is in contact with the patient's tissue based on the comparison;
    providing a notification if the sensor is determined not to be in contact with the patient's tissue; and
    determining the physiological characteristic utilizing wavelengths, other than the first wavelength, from among the three or more wavelengths if the sensor is determined to be in contact with the patient's tissue.

2. The method of claim 1, wherein comparing the intensity comprises comparing a ratio of the intensity of the detected light at the first wavelength to a reference intensity of light at the first wavelength to the threshold.

3. The method of claim 1, wherein comparing the intensity comprises comparing a ratio of the intensity of the detected light at the first wavelength to a reference intensity of the detected light at a different wavelength to the threshold.

4. The method of claim 1, wherein the first wavelength is primarily absorbed by water.

5. The method of claim 4, wherein the first wavelength is between about 1,200 nanometers to about 1,600 nanometers.

6. The method of claim 1, wherein the first wavelength is primarily absorbed by myoglobin or hemoglobin.

7. The method of claim 6, wherein the first wavelength is between about 500 nanometers to about 600 nanometers.

8. The method of claim 1, wherein the sensor comprises at least one of a sensor configured to measure tissue hydration or a pulse oximetry sensor.

9. A patient monitor, comprising:
    an I/O port configured to connect to a sensor;
    a processor configured to receive signals from the I/O port and to use the signals when executing an algorithm configured to compare an intensity of a first wavelength of detected light to a threshold, wherein the first wavelength is not used to determine a physiological characteristic of a patient, wherein the processor is also configured to execute another algorithm configured to determine if the sensor is in contact with the patient's tissue based on the comparison, and wherein the processor is further configured to provide a notification signal if the sensor is determined not to be in contact with the patient's tissue, and to determine the physiological characteristic utilizing wavelengths, other than the first wavelength, if the sensor is determined to be in contact with the patient's tissue.

10. The patient monitor of claim 9, wherein the algorithm comparing the intensity is configured, when executed by the processor, to compare a ratio of the intensity of the first wavelength of the detected light to a reference intensity of light at the first wavelength to the threshold.

11. The patient monitor of claim 9, wherein the algorithm comparing the intensity is configured, when executed by the processor, to compare a ratio of the intensity of the first wavelength of the detected light to a reference intensity of the detected light at a different wavelength to the threshold.

12. The patient monitor of claim 9, wherein the first wavelength is configured to be primarily absorbed by water.

13. The patient monitor of claim 9, wherein the first wavelength is configured to be primarily absorbed by myoglobin or hemoglobin.

14. A sensor, comprising:
one or more light emitting components configured to emit light at three or more wavelengths, wherein at least one of the wavelengths is not used to determine a physiological characteristic but is used to determine a sufficiency of contact between the sensor and a tissue of a patient based on a comparison between an intensity of detected light at the at least one wavelength and a threshold value;
one or more light detecting components configured to detect the light emitted by the one or more light emitting components;
an information encoding element that encodes the threshold value that corresponds with the at least one wavelength, wherein the threshold value, when provided to a monitor, permits the monitor to execute the comparison; and
a sensor body upon which the one or more light emitting components, the one or more light detecting components, and the information encoding element are disposed.

15. The sensor of claim 14, wherein the at least one wavelength is configured to be primarily absorbed by water.

16. The sensor of claim 14, wherein the at least one wavelength is configured to be primarily absorbed by myoglobin or hemoglobin.

17. A patient monitoring system, comprising:
a sensor comprising:
an emitter configured to emit light at three or more wavelengths into a patient's tissue; and
a detector configured to detect the light; and
a monitor configured to execute an algorithm configured to compare an intensity of a wavelength of detected light to a threshold, wherein the wavelength is not used to determine a physiological characteristic of the patient, and another algorithm configured to determine if the sensor is in contact with the patient's tissue based on the comparison, wherein the monitor is also configured to provide a notification if the sensor is determined not to be in contact with the patient's tissue, and to determine the physiological characteristic utilizing wavelengths, other than the wavelength, from among the three or more wavelengths if the sensor is determined to be in contact with the patient's tissue.

18. The patient monitoring system of claim 17, wherein the algorithm comparing the intensity is configured, when executed by the monitor, to compare a ratio of the intensity of the wavelength of the detected light to a reference intensity of light at the wavelength to the threshold.

19. The patient monitoring system of claim 17, wherein the algorithm comparing the intensity is configured, when executed by the monitor, to compare a ratio of the intensity of the wavelength of the detected light to a reference intensity of the detected light at a different wavelength to the threshold.

20. The patient monitoring system of claim 17, wherein the wavelength is configured to be primarily absorbed by water.

21. The patient monitoring system of claim 17, wherein the wavelength is configured to be primarily absorbed by myoglobin or hemoglobin.

* * * * *